United States Patent [19]

Knol et al.

[11] Patent Number: 5,491,079
[45] Date of Patent: Feb. 13, 1996

[54] **PROMOTERLESS FOREIGN GENE INTEGRATED IN *STREPTOCOCCUS THERMOPHILUS***

[75] Inventors: Jan Knol, Groningen, Netherlands; Olivier Marciset, Lausanne; Beat Mollet, Mollie-Margot, both of Switzerland

[73] Assignee: Nestec S.A., Vevey, Switzerland

[21] Appl. No.: 39,866

[22] Filed: Mar. 30, 1993

[30] Foreign Application Priority Data

Apr. 7, 1992 [EP] European Pat. Off. .............. 92105973

[51] Int. Cl.$^6$ .......................... C12N 15/09; C12N 1/13; C12P 21/00
[52] U.S. Cl. .................. 435/172.3; 435/67.1; 435/252.3; 435/253.4
[58] Field of Search ........................ 435/320.1, 252.9, 435/69.1, 172.3, 91.1, 252.3, 252.35, 253.4; 426/52

[56] References Cited

FOREIGN PATENT DOCUMENTS 0355036  2/1990  European Pat. Off. .

OTHER PUBLICATIONS

Scherer et al. (1979), Proc. Natl. Acad. Sci. USA 76(10):4951–4955.
Somkuti et al. (1988), Biochimie 70:579–585.
Weaver et al., Genetics (Wm. C. Brown Publishers, Dubuque, Iowa, 1989), pp. 196–198.
Slos et al. (1991) Appl. Environ. Microb. vol. 57(5):1333–1339.
Simons et al. (1990) Dev in Ind. Microb. vol. 31:31–39.
Herman et al. (1986) Appl. Environ. Microb. vol. 52(1);45–50.
Poolman et al. (1989) J. Bacteriol vol. 171(1):244–253.
Poolman et al. (1990) J. Bacteriol vol. 172(7):4037–4047.
Gasson, M. J., et al., 1980. Conjugal transfer of the drug resistance plasmid pAMβ in the lactic streptococci. FEMS Microbiol. Lett. 7:51–53.
Romero, D. A. et al., 1987. Conjugative mobilization as an alternative vector delivery system for lactic streptococci. Appl. Environ. Microbiol. 53:2405–2413.
Simons, G. et al., 1987. Gene expression in lactic streptococci, pp. 458–460. In O. M. Neijssel, R. R. van der Meer and K. C. A. M. Luyben (ed.), Proceeding of the 4th European Congress on Biotechnology, vol. 1, Elsevier Science Publishers B. B. Amsterdam.
Mercenier, A., et al., 1988. Development of an efficient spheroplast transformation procedure for *S. thermophilus*: the use of transfection to define a regeneration medium. Biochimie 70:567–577.
Mercenier, A., et al., 1988. Plasmid transduction in *Streptococcus thermophilus*. Mol. Gen. Genet. 212:386–389.
Somkuti, G. A., et al., 1988. Genetic transformation of *Streptococcus thermophilus* by electroporation. Biochimie 70:579–585.
Mercenier, A., et al., 1989, Genetics of *Streptococcus thermophilus*: a review. J. Dairy Sci. 72:3444–3454.
Mercenier, A., 1990. Molecular genetics of *Streptococcus thermophilus*, FEMS Microbiol. Rev. 87:61–78.
Somkuti, et al., 1991 Transfer and Expression of a Streptomyces Cholesterol Oxidase Gene in *Streptococcus thermophilus*. Biotech and Appl. Biochem. 13:238–245.
Duncan, C. H., et al., 1978. Mechanism of integrating foreign DNA during transformation of *Bacillus subtilis*. Proc. Natl. Acad. USA 75:3664–3668.
Mejean, V., et al. 1981. Rapid cloning of specific DNA fragments of *Streptococcus pneumoniae* by vector integration into the chromosome followed by endonucleolytic excision. Gene 15:289–293.
Niaudet, B. et al., 1982. Insertional mutagenesis in *Bacillus subtilis*: mechanism and use ingene cloning. Gene 19:277–284.
Gutterson, N. L., et al., 1983 Replacement and amplification of bacterial genes with sequences altered in vitro. Proc. Natl. Acad. Sci. USA 8:4894–4898.
Raibaud, O., et al., 1984. A technique for integrating any DNA fragment into the chromosome of *Escherichia coli*. Gene 29:231–241.
Chopin, M. C., et al., 1989. Insertion and amplification of foregin genes in the *Lactococcus lactis* subsp. lactis chromosome. Appl. Environ. Microbiol. 55:1769–1774.
Leenhouts, K. J., et al., 1989. Campbell–like integration of heterologous plasmid DNA into the chromosome of *Lactococcus lactis* subsp. lactis. Appl. Environ. Microbiol. 55:394–400.
Resnik, E., et al., 1991. Introduction of single–copy sequences into the chromosome of *Escherichia coli*: application to gene and operon fusions. Gene 107:19–25.
Sato, Y., et al., 1992, Cloning of the phospho–β–galactosidase gene in *Escherichia coli* from lactose–negative mutants of *Streptococcus mutans* isolated following random mutagenesis with plasmid pVA891 clone banks. FEMS Microbiol. Lett. 91:219–224.

Primary Examiner—Mindy Fleisher
Assistant Examiner—Philip W. Carter
Attorney, Agent, or Firm—Vogt & O'Donnell

[57] ABSTRACT

A promoterless foreign gene is intergrated into the lac operon of *Streptococcus thermophilus* by transforming a host strain of *Streptococcus thermophilus* with a donor plasmid which does not replicate in the host strain. The donor plasmid includes a vector backbone and a sequence containing a foreign gene operably intergrated into at least a part of the lac operon of the host strain, in front of at least a part of the lacZ gene of the lac operon, and the sequence conserves the frame of the genomic lac operon of the host strain. Cointegrate transformants are identified in which the complete donor plasmid is integrated into the geonomic lac operon of the host strain, and an integrant transformant is then selected, the genome of which does not include the vector backbone of the donor plasmid but does include the foreign gene, which is operably integrated in front of the lacZ gene of the conserved genomic lac operon and which is stably maintained and expressed upon selective pressure on expression of the lacZ gene.

6 Claims, 7 Drawing Sheets

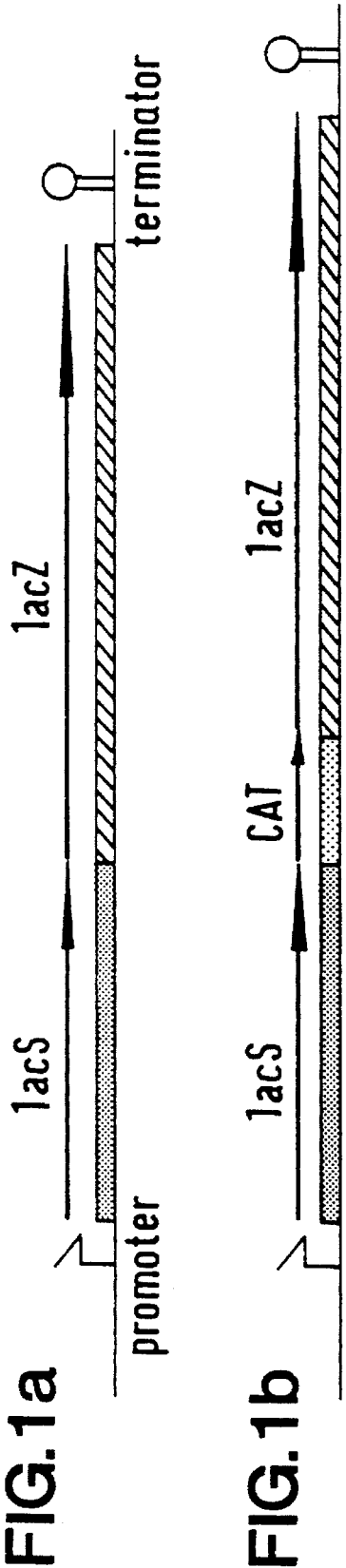
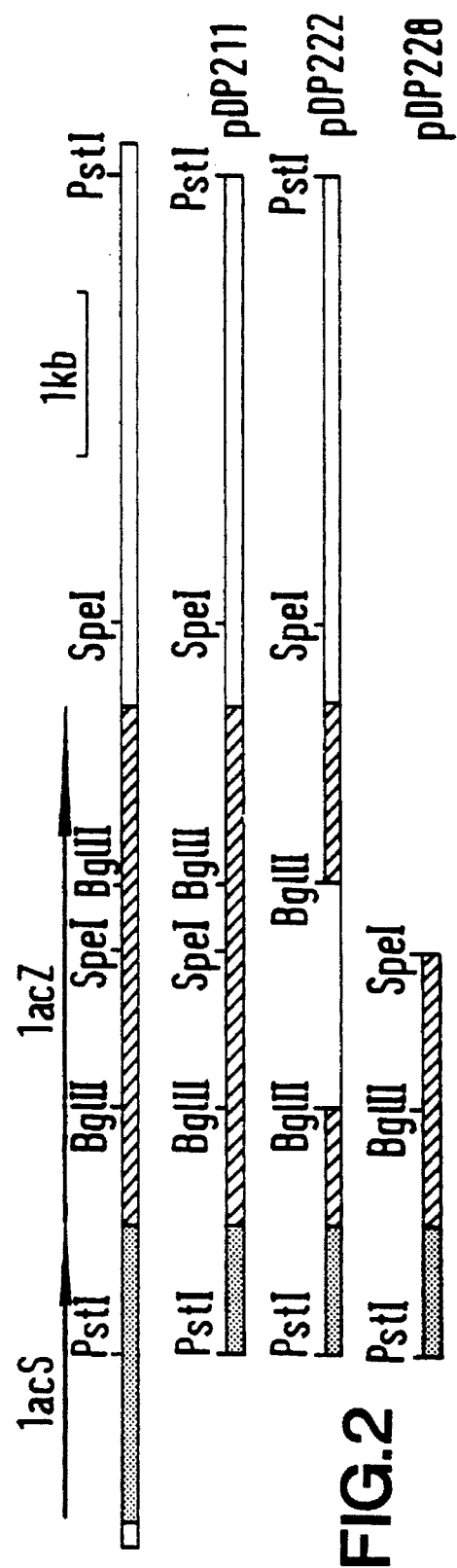
FIG. 1a
FIG. 1b
FIG. 2

FIG.6
pDP228
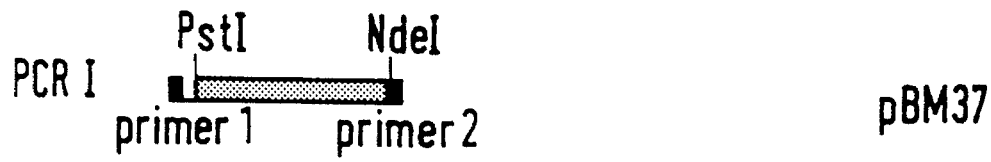
pBM37
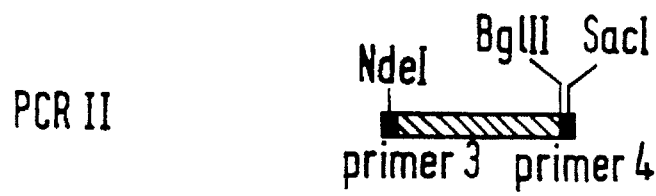
pBM38
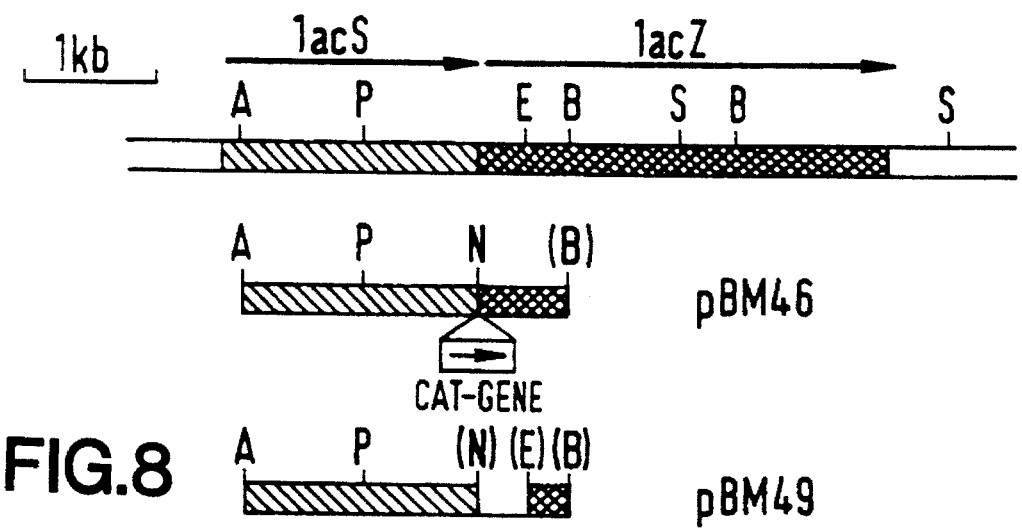
FIG.8

PROMOTERLESS FOREIGN GENE INTEGRATED IN STREPTOCOCCUS THERMOPHILUS

BACKGROUND OF THE INVENTION

The present invention relates to a food-grade gene integration and expression system in microorganisms, especially in *Streptococccus thermophilus* or in *Lactobacillus bulgaricus*. Maintenance and expression of any homologous and/or heterologous gene is selected for indirectly by simply growing the cells in their natural habitat, especially milk.

STATE OF THE ART

*Streptococcus thermophilus* (*S.thermophilus*) is a very important microorganism for the fermentation of food. It is predominantly used in the fermentation of milk products where it is particularly used as starter culture, often in combination with other homo- or heterofermentative bacteria, for yogurt and cheese production. Only recently, progress has been made in the genetics of this organism. Several gene transfer techniques as conjugation [Gasson, et al. 1980. Fed. Eur. Microbiol. Soc. Microbiol. Lett. 7:51–53; Romero, et al. 1987. Appl. Environ. Microbiol. 53:2405–2413], transfection [Mercenier, et al. 1989. Biochimie 70:567–577] and transformation [Mercenier, et al. 1988. Mol. Gen. Gent. 212:386–389; Somkuti, et al. 1988. Biochimie 70:579–585] have been reported for this species. So far, this enabled the examination and use of already existing bacterial plasmids as cloning vectors [Mercenier, et al. 1989. Biochimie 70:567,577; Somkuti, et al.1988. Biochimie 70:579–585] as well as a beginning in designing new vector systems [Slos, et al. 1991. Appl. Environ. Miccrobol. 57:133–1339]. Although very little is known about transcriptional and translational control regions in *S. thermophilus* [Mercenier, et al. J. Dairy Sci. 72:3444–3454], expression of some heterologous genes, delivered and maintained on plasmids, was reported [Somkuti, et al. 1991. Biotech. and appl. Biochem. 13:238–245]. However, expression levels are not predictable and often low or not detectable [Mercenier, et al. J. Dairy Sci. 72:344–3454].

Plasmids are not a priori segregated in a stable way and may be lost under nonselective growth conditions. This may in particular be true for plasmid systems which are genetically engineered and carry heterologous DNA. Selection applied for ensuring plasmid maintenance make in most cases use of marker genes referring resistance to antibiotics. Although very convenient for laboratory scale experiments, such a selection system can not be applied in food production. Up to date, a food grade gene transfer system for *S. thermophilus* has not been reported.

OBJECTS OF THE INVENTION

A first object of the present invention is to provide a process for integrating a foreign gene into the chromosomal DNA of a food-grade microorganism, especially into the chromosomal DNA of *Streptococccus thermophilus* or of *Lactobacillus bulgaricus*, in such a way as to ensure the maintenance and expression of the gene by indirect selection upon growth of the cells in their standard medium, especially milk.

A second object of the present invention is to provide a process of integration which is food-grade (without taking the gene to be integrated into consideration).

A third object of the present invention is to provide a process of integration which does not make it necessary to directly select for the function of the foreign gene to be integrated and expressed at any step of the construction process.

A fourth object of the present invention is to provide a genetically modified microorganism obtained by such a process.

A fifth object of the present invention is to provide a derivative copy of a microorganism for carrying out such a process.

A sixth object of the present invention is to provide a donor plasmid for carrying out such a process.

A seventh object of the present invention is to provide a fermentation process, in which a food-grade substrate is fermented with such a genetically modified microorganism.

An eigth object of the present invention is to provide a food product or a food additive obtained by such a fermentation process.

SUMMARY OF THE INVENTION

In accordance with the present invention, there is provided a process for integrating a promoter-less foreign gene into an operon in front of at least one essential cistron on the DNA of a food-grade microorganism, in such a way that the gene is expressed as functional part of this operon and that the gene is stably maintained and expressed due to selective pressure on correct functioning of the essential cistron upon growth in standard medium.

BRIEF DESCRIPTION OF THE DRAWINGS

FIG. 1 illustrates the gene organization of the lac operon in *S. thermophilus*. FIG. 1(*a*) represents the lac operon of the wild type ST11 and FIG. 1(*b*) represents the one of ST11-Cat. lacS and lacZ indicate the genes encoding lactose permease and β-galactosidase, respectively. The promoter and terminator are indicated.

FIG. 2 is a physical map of the clones carrying parts of the lac operon. Restriction sites used for cloning are indicated.

FIG. 3(*a*) displays the modification generating a NdeI restriction site between the lacS and lacZ gene. Asterisks (*) indicate the mutated base pairs. FIG. 3(*b*) represents the in vitro insertion of the cat gene into the generated NdeI site.

FIG. 4(*a*) represents the integration event of a plasmid into the chromosome via homologous recombination. FIG. 4(*b*) shows the resolution of a chromosomal cointegrate via homologous recombination, leaving the modified copy of the operon back on the chromosome. The erythromycin resistance marker, ery, located on the plasmid backbone, is indicated.

FIG. 6 outlines the construction of pBM38. Primers used for PCR are indicated outsized. Restriction sites used for cloning are indicated.

FIG. 7 includes physical maps of pBM45 cointegrates and resolution end products.

FIG. 8 includes physical maps of the constructed plasmids. Restriction sites are: A, AatII, P, PstI; E, EcoRI; S, SpeI; B, BglII; N, NdeI. Only the EcoRI site used for constructing pBM49 is indicated. Restriction sites shown in brackets were truncated by the cloning procedure.

FIG. 9 illustrates integration of the cat gene into the genome of ST11-ΔlacZ.

Figures 3A, 3B:
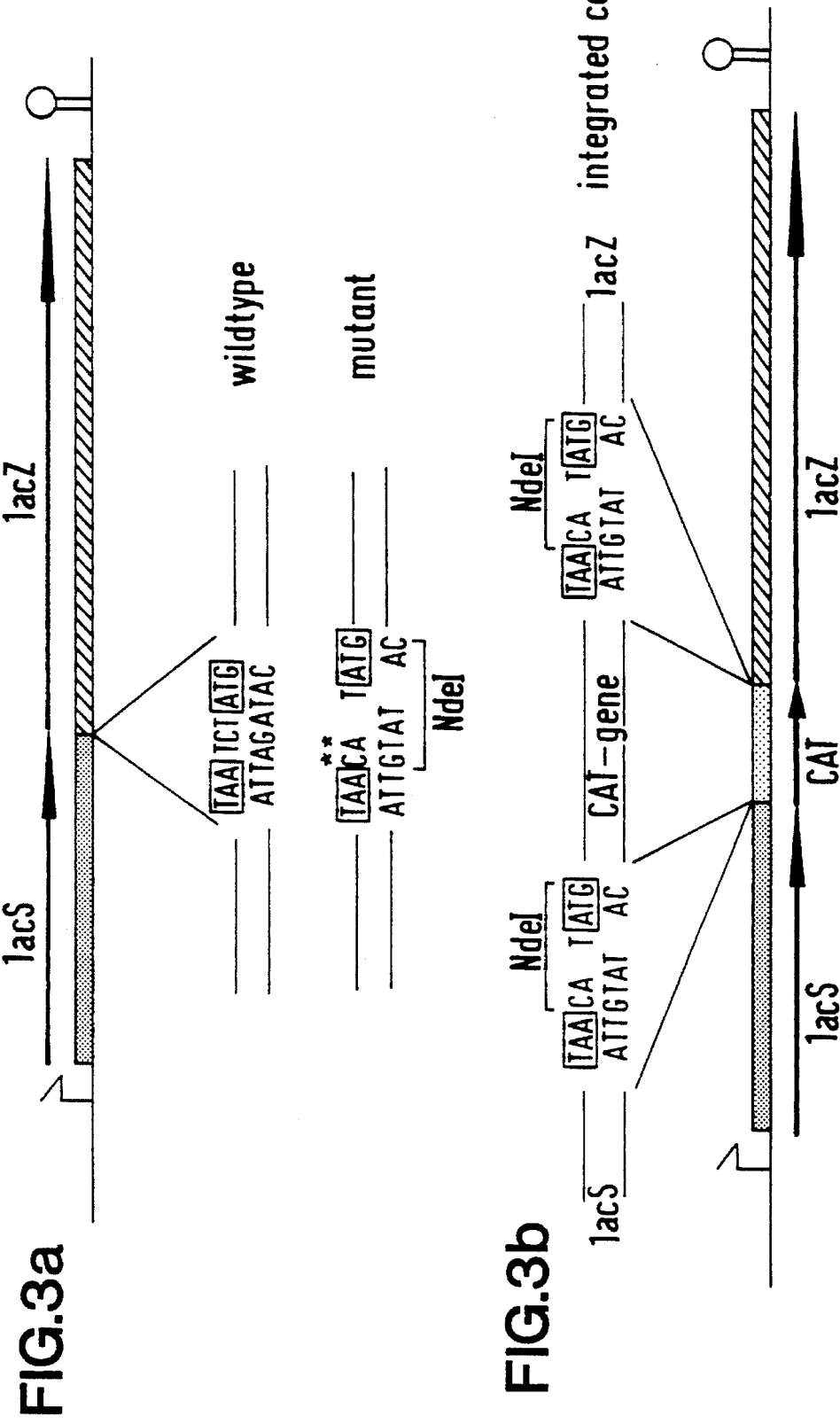
FIG. 3 is a schematic representation of the genetic construction.

Preferably, this process comprises transforming said microorganism with a donor plasmid which is not able to replicate by itself in the microorganism and which carries said foreign gene as a functional part of said operon in front of said essential cistron.

Preferably, this process further comprises isolating transformants containing plasmid-genome cointegrates and resolving the cointegrates to achieve correct integration of the foreign gene.

Also preferably, said microorganism is a lactic acid bacterium selected from a group comprising the genera Streptococcus, Lactococcus, Lactobacillus, Leuconostoc, Pediococcus, Enterococcus and Bifidobacterium, and the food-grade strains of the genera Propionibacterium and Staphylococcus.

More preferably, said microorganism is *Streptococcus thermophilus* or *Lactobacillus bulgaricus*.

Also preferably, said plasmid is derived from a plasmid carrying the whole or part of said operon.

Furthermore, said donor plasmid preferably is able to replicate itself in another host system than said microorganism and it further carries a selectable gene marker which is functional in said microorganism as well as in said other host system.

Said other host system may be *E.coli*, for example.

In a preferred embodiment of the present invention, said operon is the lac operon and said essential cistron is the lacZ gene. In this embodiment, said donor plasmid may be obtained by modifying the wildtype sequence of said operon lac to generate a NdeI restriction site between the lacS and lacZ genes and inserting said foreign gene into the generated NdeI site.

The process according to the present invention may also comprise transforming said microorganism by electroporation.

In another preferred embodiment of the present invention, the present process may further comprise preparing a derivative copy of said microorganism having a deletion within said essential cistron, this deletion being completed during the transformation and allowing simplified resolution of said cointegrates.

DETAILED DESCRIPTION OF THE INVENTION

The principle of the present invention is to integrate a foreign gene into a vital operon of the genome of a food-grade microorganism, especially *S.thermophilus*, for example, in such a way to preserve the correct functioning, i.e. transcription and translation, of the operon and to have the heterologous gene as an integrative, functional part of the operon. In order to ensure correct expression of the integrated gene, it should be placed in front of an essential gene (cistron) of the same operon. Thus, selective pressure on the essential gene during cell growth under normal conditions in standard medium, e.g. in milk, ensures genetic maintenance and expression of the integrated gene. According to what operon is chosen as carrier system, different levels of expression and/or possibilities of regulation can be adopted.

The present invention bears the following advantages over reported gene transfer systems in food-grade microorganisms, especially in *S.thermophilus*, for example:

It is homogenic and food-grade (without taking the foreign gene to be expressed into consideration).

The integration of a gene into the genome is stable. It follows the strict copy number control of the host cell genome.

Expression of the gene is controlled by a host cell proper promoter system.

Any foreign gene of homogenic, heterogenic, or synthetic origin, or of a combination thereof, can be expressed without the need for direct selection, observable phenotype or adaptation of the growth medium.

Selection on the maintenance and expression of the gene is indirect upon growth of the cells in their standard medium, e.g. a milk based medium, especially milk, milk permeate or whey.

It may be noticed here that, throughout the present specification and claims, the expression "foreign gene" is to be understood as meaning any homologous, heterologous or artificial stretch of DNA coding for any useful product, such as an enzyme, for example.

In order to achieve integrative gene expression in a food-grade microorganism, especially in *S.thermophilus*, for example, the following steps may be taken:

Designing of a donor plasmid. To directly select for integration events in *S. thermophilus*, the donor plasmid should not be able to replicate by itself. It should carry a selectable gene marker which is functional in *S. thermophilus* and contain a stretch of DNA, homologous to the *S. thermophilus* genome. Preferentially, the donor plasmid can replicate in an other host system than *S. thermophilus*, e.g. *E. coli*, for convenient genetical engineering and plasmid proliferation.

Targeting of integration. Integration of the donor plasmid occurs via recombination between homologous stretches of DNA of the donor plasmid and the genome of *S. thermophilus*. The donor plasmid which carries the gene to be integrated, has to be engineered in such a way to ensure proper integration of the gene into the operon. Upon integration, a genetical configuration, designated as cointegrate, is formed between the genome and the donor plasmid.

Optimization of the transformation procedure for *S. thermophilus*. In order to get detectable integration events, the transformation frequency (i.e. the number of transformants per μg of input plasmid DNA) has to be reasonably high. Up to date reported transformation procedures were not sufficient to detect integration events. Therefore, we optimized the procedure for *S. thermophilus* by using the electroporation technique.

Genome integration. Integration of genes, or parts thereof, from donor plasmids onto the genome of *S. thermophilus* has not been reported yet. With our optimized transformation protocol we were able to reproducibly isolate 1–10 integrants per 1 μg of input plasmid DNA. Each integration event resulted in the formation of a cointegrate.

Resolution of the cointegrates. Upon release of the plasmid based selection system, a host cell proper recombination system tends to resolve the cointegrate structure and, thus, to eliminate the vector backbone of the donor plasmid. DNA sequences originating from *E. coli* and antibiotic resistance markers will be lost. In order to pick the desired final construction amongst the different possible resolution end products, individual descendents of the transformants have to be screened for by using DNA hybridization techniques [SOUTHERN E. 1975. J. Mol. Biol. 98:503–517]. (Example 1), or they can be selected for directly by using an appropriatly designed host strain for integration (Example 2).

The feasibility of the above described procedure was demonstrated by integrating a promoter-less chloramphenicol acetyl transferase (cat) gene, derived from *Lactococcus lactis* plasmid pNZ12 [Simons G., et al. 1987. Proc. 4th European Congress on Biotechnology, Vol. 1, p:458–460], into the lac operon of *S. thermophilus* between the two genes lacS and lacZ [Herman R. E., et al. 1986. Appl. Environ. Microbiol. 52:45–50; Poolman B., et al. 1989. J.Bacteriol. 171:244–253; Poolman B., et al 1990. J. Bacteriol. 172:4037–4047]. The gene organization of the modified operon which now replaces the original lac operon on the *S. thermophilus* genome is shown in FIG. 1. Analysis of independent cultures after growth in milk for more than 100 generations (without selection on chloramphenicol) indicated that the cat gene was durably maintained. Furthermore, expression and regulation of the cat gene was shown to be parallel to that of the β-galactosidase (lacZ) gene, which is vital for growth of *S. thermophilus* in milk.

DEPOSIT OF BIOLOGICAL MATERIAL

The plasmid pBM46 was deposited pursuant to the Budapest Treaty on AUG. 17, 1995, in the Collection Nationale de Cultures de Microorganismes (CNCM), Institut Pasteur, 28 rue du Dr. Roux, 75724 Paris Cédex 15, France, where it was given the number CNCM I-1619.

EXAMPLES

Bacterial and plasmids *S. thermonhilus* ST11, a starter strain for yogurt production, is from our collection. It was deposited under the Budapest treaty on the 29.03.93 in the Collection Nationale de Cultures de Microorganismes (CNCN) de l'Institut Pasteur, 25 rue de Docteur Roux, 75724 Paris Cedex 15, France, where it was given the number I-1292. *E. coli* strains used were BZ234 (collection from the Biozenter, University of Basel, Switzerland) and JM108 [Yanisch-Perron C., et al. 1985. Gene 33:103–119]. Plasmids were: pVA838 [Macrina F. L., et al. 1982. Gene 19:345–353], pNZ12 [Simons G., et al. 1987. Proc. 4th European Congress on Biotechnology, Vol. 1, P:458–460], pGEM-5Zf (Promega, U.S.A.), pUC-838-1 (pUC18 [Yanisch-Perron C., et al. 1985. Gene 33:103–119] having the 1.7 HindIII-AvaI fragment with the erythromycin resistance gene (Em$^r$) pVA838 bluntended and inserted into the unique SmaI site), pGEM5-838-2 (pGEM-5Zf carrying the identical 1.7 kb fragment from pVA838 as pUC-838-1 bluntended and inserted into the unique EcoRV site), pDP211 (pUC19 [Yanisch-Perron C., et al. 1985. Gene 33:103–119]having the 7.0 kb PstI fragment carrying the lacZ gene from *S. thermophilus* ST11 cloned into the unique PstI site (similar construction as pRH116 [Herman R. E., et al. 1986Appl. Environ. Microbiol 52:45–50])), pDP222 pDP211 having the latz internal 1.3 kb BglII fragment deleted by cutting with BglII and subsequent religation), pDP228 (pUC19 having the 2.4 kb PstI-SpeI fragment from pDP211 cloned into its unique PstI and SpeI sites) and pDP301 (pKK223-3 [Pharmacia Inc., U.S.A.]. having the 4.2 kb EcoRI fragment carrying the lacS gene from ST11 cloned into the unique EcoRI site (identical construction as pEKS8 [Poolman B. et al. 1989. J. Bacteriol. 171:244–253])) (FIG. 2). Plasmid pUC-838-1 was received from B. Suri, Ciba-Geigy Ltd., Switzerland, and plasmid pGEM5-838-2, pDP211, pDP222, pDP228 and pDP301 were received from D. Pridmore, Nestec Ltd., Switzerland.

*S. thermophilus* was grown in HJL (3% tryptone, 1% yeast extract, 0.5% $KH_2PO_4$, 0.5% beef extract and 1% lactose), M17 broth (Difco Laboratories) and MSK (9% reconstituted skim milk powder supplemented with 0.1% yeast extract). Where indicated, media were supplemented with 1% glucose, 1% lactose or 1% sucrose. *E. coli* strains were grown in LB (0.5% NaCl, 1% tryptone, 1% yeast extract). Media were solidified for plating by the addition of 1.5% agar. Erythromycin, chloramphenicol, ampicillin, X-gal (5-bromo-4-chloro-3-indolyl-β-D-galactopyranoside) and IPTG (isopropyl β-D-thiogalactopyranoside) were added individually as indicated.

Preparation of DNA
1) Plasmid DNA from *E. coli*.

Plasmid DNA from *E. coli* was isolated and as needed purified on CsCl gradients according to Maniatis et al. [Maniatis T., et al 1982. Molecular Cloning: A Laboratory Manual. Cold Spring Harbor Laboratory, Cold Spring Harbor N.Y.].

2) Genomic DNA from *S. thermophilus*.

Cells were grown overnight in 15 ml HJL broth supplemented with 1% glucose at 42° C. in anaerobiosis (Anaerobic Systems, BBL GasPak, Becton Dickinson & Co.). The cells were then harvested by centrifugation and washed once in 1M NaCl. Genomic DNA was isolated as reported by Delley et al. [Delley M., et al. 1990. Appl. Environ. Microbiol. 56:1967–1970] and stored at 4° C.

Transformation procedure for *S. thermophilus* ST11

Plasmids used to optimize transformation for *S. thermophilus* ST11 were pVA838 and pNZ12. They both replicate in *E. coli* as well as in *S. thermophilus* and their antibiotic resistance marker, erythromycin and chloramphenicol, respectively, are functional in both host systems for appropriate selection. As transformation method we used electroporation. The following parameters were considered and optimized: growth of the host cells, preparation of the cells, parameters of electropulsing, buffer composition for pulsing, expression and plating of transformed cells. The optimized procedure is described below.

*S. thermophilus* ST11 was grown in HJL medium supplemented with glucose overnight at 42° C. The next day, 33 ml of identical fresh medium was inoculated with 700 μl of the overnight culture and grown for 1–3 generations (maximal $OD_{600}$ =0.3) at 42° C. The cells were harvested by centrifugation (5 min at 2000 g), washed once with 5 mM $KPO_4$ buffer (pH 7), resuspended gently in freshly prepared ice cold EPM to an exact OD$_{600}$ of 0.9 (EPM: 0.3M raffinose, 5 mM KPO$_4$ buffer (pH 6.1), 0.5 mM MgCl$_2$) and kept on ice at 0° C. 200 µl of cell suspension was added to a prechilled (0° C.) 0.2 cm electroporation cuvette containing 1 µg of plasmid DNA, mixed and electroporated with the Gene pulser apparatus (Bio-Rad Laboratories, U.S.A.) at 25 µF, 400Ω and 2.05 kV. Immediately after pulsing, 1 ml of 1.2 times concentrated M17, supplemented with sucrose, was added to the cuvette, mixed with the cells, transferred to a sterile tube and incubated at 42° C. for 4 hours. Then, 4 ml of melted soft agar (M17 supplemented with sucrose and 0.6% agar) was added to the culture and the mix plated onto a M17 agar plate containing sucrose and 2.5 µg/ml erythromycin (for plasmid pVA838) or 2.5 µg/ml chloramphenicol (for plasmid pNZ12). The plate was incubated at 42° C. for 2–3 days under anaerobic conditions (BBL GasPak, Becton Dickinson & Co.).

DNA-DNA hybridization

Genomic DNA of *S. thermophilus* was digested with appropriate restriction enzymes, fractionated by agarose gel electrophoresis and transferred to GeneScreen membranes. Southern blot hybridizations were performed as described by Southern [Southern E. 1975. J. Mol. Biol. 98:503–517]. DNA probes were $^{32}$P labeled by the random priming method [Maniatis T., et a. 1982. Molecular Cloning: A Laboratory Manual. Cold Spring Harbor Laboratory, Cold Spring Harbor, N.Y.]. Alternatively, we used a non radioactive, enhanced chemiluminescence labelling method for the DNA probes (ECL system, Amersham). Hybridization and washing of the blots were performed under stringent conditions.

Other DNA manipulations

Agarose gel electrophoresis, restriction enzyme digestions, ligations, alkaline phosphatase treatments and transformation of *E. coli* strains were performed according to standard procedures [Manitis T., et a. 1982. Molecular Cloning: A Laboratory Manual. Cold Spring Harbor Laboratory, Cold Spring Harbor, N.Y.]. Synthetic oligonucleotides were prepared by D. Pridmore (Nestec Ltd., Switzerland) on an Applied Biosystems 380B DNA synthesizer and purified on Nap-10 gel filtration columns from Pharmacia LKB. PCR was performed according to Saiki et al. [Saiki R. K., et al. 1985. Science 230:1350–1354; Saikai R. K., et al. 1988. Science 239:487–491].

EXAMPLE 1

Integration of the cat gene into the lac operon

The lac operon of *S. thermophilus* is located on the bacterial genome and consists of two genes, the lactose permease (lacS) and the β-galactosidase (lacZ) gene. They are separated by only 3 bp [Poolman B., et al. 1989. J. Bacteriol. 171:244–253]. It is our intention to integrate a "foreign" gene into this operon, between the lacS and lacZ gene in such a way to have an identical spacing, i.e. 3 bp between each of the 3 genes and, thus, to conserve the properties of the operon. Selective pressure on expression of the lacZ gene ensures expression of the two other genes. Furthermore, host mediated spontaneous deletions or rearrangements in or at the "foreign" gene locus will in most cases affect the correct functioning of the operon and, thus, be eliminated by the selection for lacZ activity.

As a model gene for integration, we chose the chloramphenicol acetyl transferase (cat) gene. Integrative gene expression of this gene should render the host cells, i.e. *S. thermophilus*, resistent to the antibiotic chloramphenicol, which can be tested and monitored easily along the different experimental steps. Furthermore, convenient assays exist to determine quantitatively the level of expressed chloramphenicol acetyl transferase [Shaw W. V. 1975. Meth. Enzymol. 43:737–755].

In order to make the appropriate genetical constructions, a part of the laC operon containing the junction region of the lacS and lacZ gene was isolated and cloned in *E. coli*. By in vitro mutagenesis, making use of the PCR technology, we introduced a NdeI restriction site, which recognizes the sequence CA/TATG, right in front of the lacZ gene, overlapping with its ATG start codon (FIG. 3a). The spacing of the two genes stayed intact and the sequence alterations were within the spacing region and did not affect the primary sequence of the genes. Then, we PCR amplified the cat gene from the *Lc. lactis* plasmid pNZ12 with primers introducing a NdeI site at the start, overlapping with the ATG start codon, and at the end of the gene, located immediately after the TAA stop codon. The amplified cat gene was inserted at its new NdeI sites into the newly created NdeI site between the lacs and lacZ gene, thus, generating the desired new operon structure, now consisting of three perfectly arranged genes (FIG. 3b).

Figure 4A:
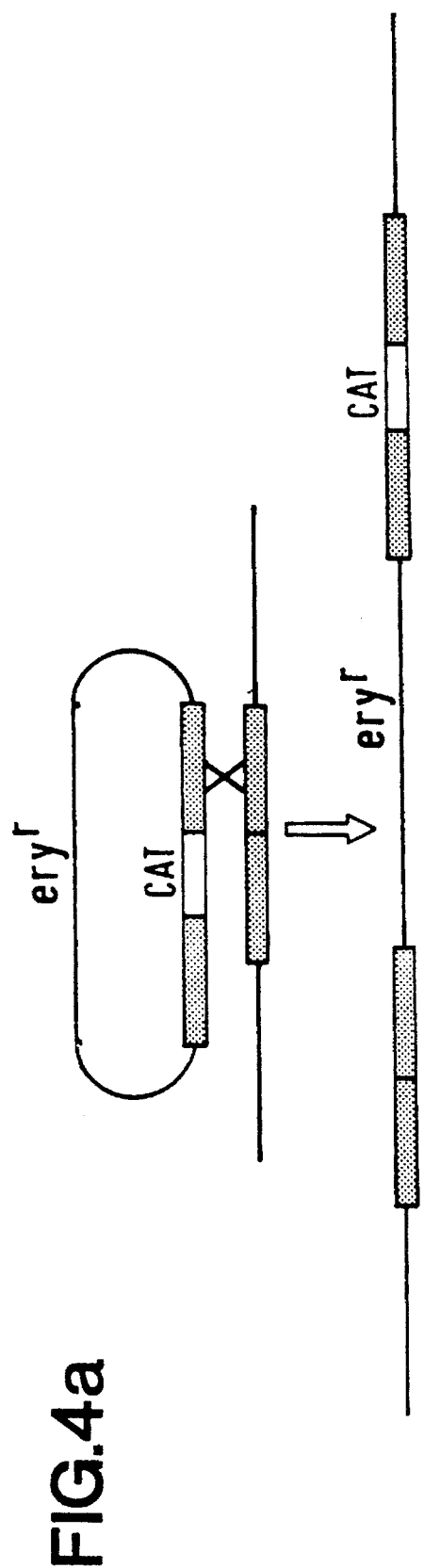
FIG. 4 illustrates chromosomal integration and resolution.
Figure 4B:
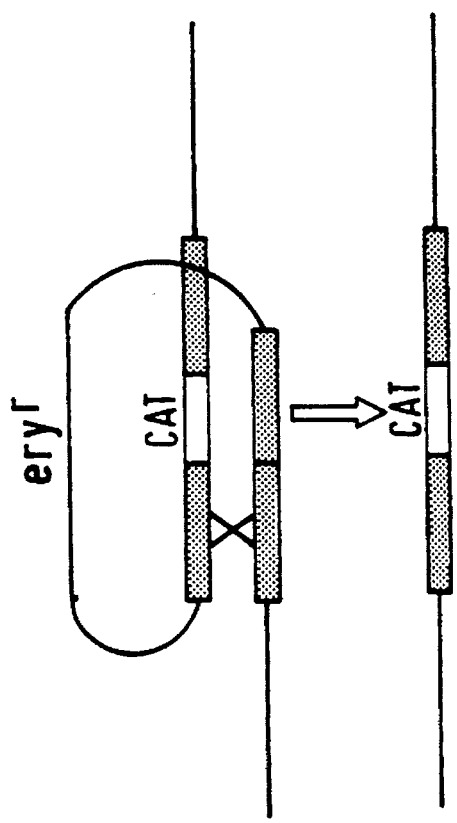

Plasmids containing the construction with the integrated car gene were transformed into *S. thermophilus*. As the plasmids can not autonomously replicate in this host system, they could not be maintained as plasmids and were aborted. Upon appropriate selection, however, rare integration events of plasmids into the host cell genome, where they were maintained and replicated passively, could be observed and isolated. Selection of integration events was based on the plasmid encoded erythromycin resistance gene and resulted in the isolation of cointegrates between the bacterial genome and the plasmids formed by a single recombination event (FIG. 4a). Appropriate resolution of the cointegrates upon release of the erythromycin selection pressure (second recombination event) resulted in a perfect replacement of the original lac region by the one introduced on the donor plasmid (FIG. 4b). Expression levels and stability of the integrated cat gene can be tested directly.

Construction of donor plasmids i) pBM20, pBM26 and pBM33

Figure 5:
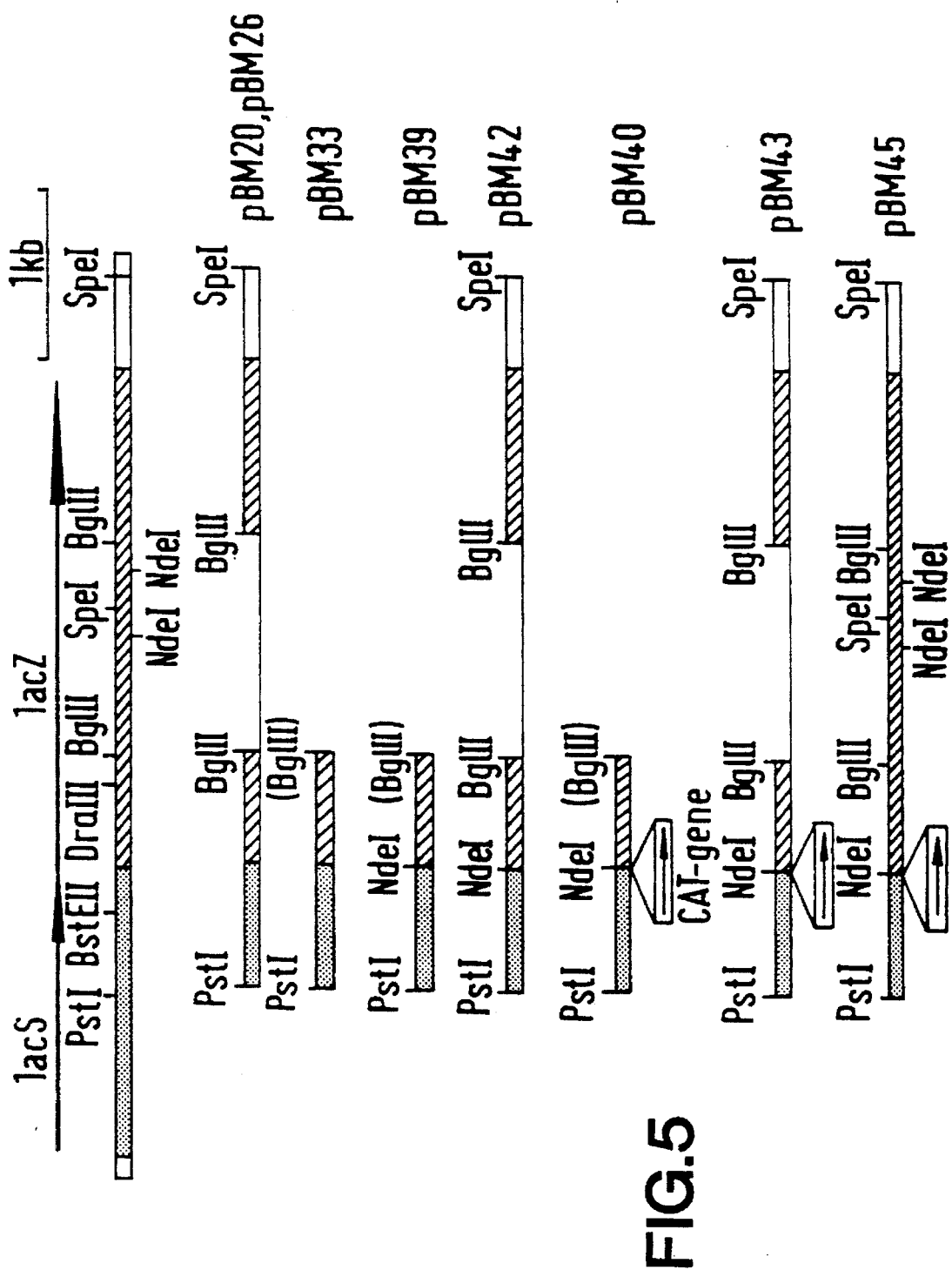
FIG. 5 is a physical map of the constructed plasmids. Restriction sites are indicated. A BglII site in brackets indicates that it was truncated by cloning into a BamHI site of the vector plasmid. The orientation of the cat gene is shown by arrow.

The PstI-SpeI fragment of pDP222 containing the truncated lacZ gene was ligated into vector pGEM5-838-2 linearized at its unique PstI and SpeI sites and transformed to *E. coli* BZ234. The cells were plated on LB plates supplemented with 1 mg/ml erythromycin and grown at 37° C. overnight. Single colonies were isolated and grown in LB supplemented with 100 µg/ml ampicillin. Plasmid DNA was extracted and analyzed by restriction site mapping. Plasmids carrying the correct fragment were identified and named pBM20 (FIG. 5). In order to shorten the vector backbone and to eliminate the ampicillin resistance gene, pBM20 was digested with FspI (which cuts at position 1617 and 2843 in pGEM5 [Promega, U.S.A.]), religated and transformed to BZ234. Selection was on identical LB erythromycin plates as above. Plasmids having the correct 1.2 kb FspI deletion were identified and named pBM26.

Alternatively, vector pUC-838-1 was FspI digested, religated and transformed to BZ234 as described above. The resulting vector, named pBM31, was linearized at its unique EcoRI site, the ends bluntended by a filling-in reaction [Maniatis T., et al. 1982. Molecular Cloning: A Laboratory Manual. Cold Spring Harbor Laboratory, Cold Spring Harbor, N.Y.], ligated and transformed to BZ234. The new vector, named pBM32, was linearized at its unique PstI and BamHI site, and ligated to the by agarose gel electrophoresis purified 1.55 kb PstI-BglII fragment from pBM20. The ligation mix was transformed to BZ234, the cells plated and grown on LB erythromycin (1 mg/ml) agar plates. The plasmid content of single colonies was analyzed, the correct clones identified and named pBM33 (FIG. 5).

ii) pBM39 and pBM42

A NdeI restriction site between the lacS and lacZ gene was generated as outlined in FIG. 6. A ca. 900 bp long fragment containing the C-terminal end of lacS was PCR amplified from FspI linearized pDP228. The synthetic oligonucleotides used as primers were 5'-GGTTTTCCCAGT-CACGAC (primer 1, hybridizing to vector pUC19[SEQ ID NO:1]) and 5'-GTCATGTTCATATGTTATTCTCCTTT (primer 2, introducing a NdeI site [SEQ ID NO:2]). The amplified fragment was PstI and NdeI digested, and ligated to the PstI and NdeI digested vector pGEM-5Zf, transformed to BZ234 and the cells selected for growth on LB ampicillin (100 μg/ml) plates. The plasmid content of single colonies was analyzed, correct clones carrying the 900 bp fragment identified and named pBM37. A second PCR was carried out from the linearized pDP228 with using the synthetic oligonucleotides 5'-AAAGGAGAATAACATAT-GAACATGAC (primer 3[SEQ ID NO:3]) and 5-TTGG-GAGCTCTCCCTTAACAAAGAGA (primer 4, containing a SacI site next to the BglII site). The ca. 700 bp amplified fragment was digested with SacI and NdeI, and ligated into the SacI and NdeI digested pBM37. The ligation mix was transformed to BZ234 and the cells grown on LB ampicillin (100 μg/ml) plates. The plasmid content of single colonies was analyzed, correct clones containing the insert identified and named pBM38.

Plasmid pBM38 was digested with BstEII and DraIII, and the resulting 650 bp fragment, containing the new junction between the lacS and lacZ gene, isolated by agarose gel electrophoresis. Similarly, pBM33 and pBM26 were digested with BstEII and DraIII, and their larger fragment containing the vector backbone isolated and each ligated to the 650 bp fragment from pBM38. Ligation mixes were transformed to BZ234, plated onto LB erythromycin (1 mg/ml) plates and incubated at 37° C. The plasmid content of single colonies was analyzed and correct clones carrying the inserted NdeI site transferred from pBM38 were identified. Plasmids originating from pBM33 and pBM26 were named pBM39 and pBM42, respectively (FIG. 5).

iii)pBM40, pBM43 and pBM45

The cat gene from pNZ12, which was first linearized at its unique salI site, was PCR amplified. The synthetic oligonucleotides used as primers to generate NdeI sites at the start and end of the cat gene were 5'-ATATCATATGAACTT-TAATAAAATTGAT [SEQ ID NO:5] and 5'-ATTATCATAT-GTTATAAAAGCCAGTCATTAG [SEQ ID NO:6]. The ca. 670 bp long amplified fragment was digested with NdeI and ligated into pBM39 which was linearized at its unique NdeI site and alkaline phosphatase treated. The ligation mix was transformed to BZ234, plated onto LB erythromycin (1 mg/ml) plates and incubated at 37° C. The plasmid content of individual colonies was analyzed and clones, having the NdeI fragment inserted in the correct orientation, i.e. the cat gene reading in the same direction as lacS and lacZ, identified and named pBM40 (FIG. 5).

Plasmid pBM40 was digested with BstEII and DraIII, and the 1.3 kb fragment containing the cat gene isolated by agarose gel electrophoresis. Similarly, pBM26 was digested with BstEII and DraIII, and the fragment containing the vector backbone was isolated. The two isolated fragments were ligated together, transformed to BZ234 and the cells grown on LB erythromycin (1 mg/ml) plates. The plasmid content of single colonies was analyzed, correct clones identified and named pBM43 (FIG. 5).

Plasmid pDP211 was digested with BglII and the 1.3 kb lacZ internal fragment isolated by agarose gel electrophoresis. This fragment was ligated into pBM43, which was first linearized at its BglII site and alkaline phosphatase treated. The ligation mix was transformed to JM108 and plated onto LB plates supplemented with 1 mg/ml erythromycin, 40 μg/ml X-gal and 1 mM IPTG. The cells were grown at 37° C. overnight. The plasmid content of individual blue colonies (LacZ$^+$; [Miller J. H. 1972. Experiments in Molecular Genetics. Cold Spring Harbor Laboratory, Cold Spring Harbor, N.Y.]) was isolated and analyzed. Correct clones carrying the entire lacZ gene were identified and named pBM45 (FIG. 5).

Integration of the cat gene into the genome of ST11 i) cointegrate formation

Figure 7A:
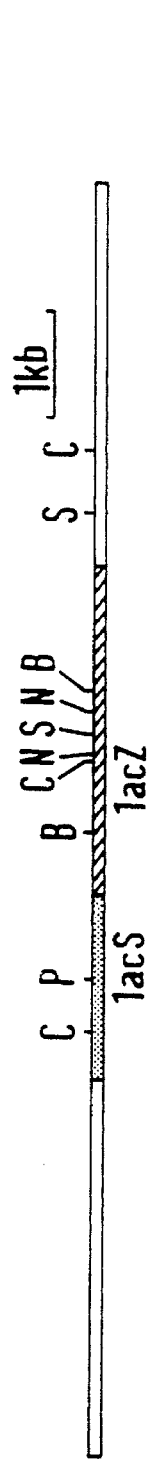
FIG. 7(a) shows the restriction map of the lac operon of ST11.
Figure 7B:
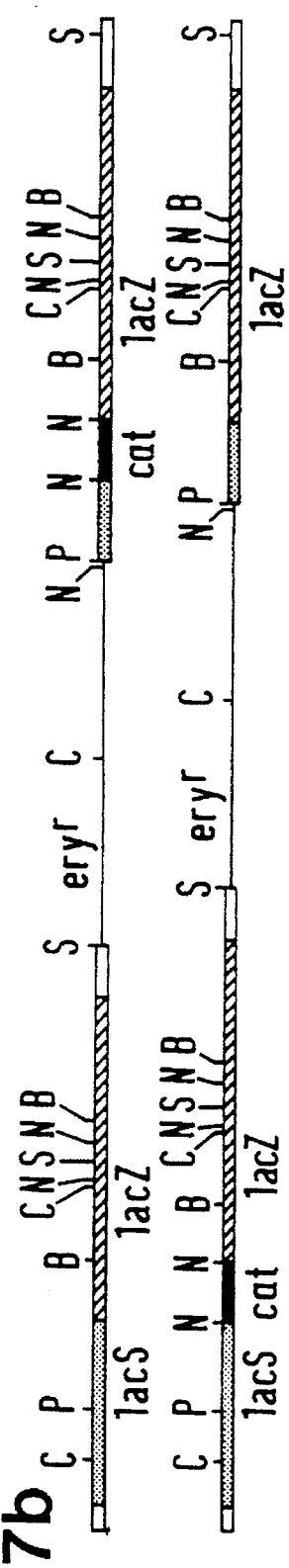
FIG. 7(b) illustrates the ones of the two possible, identified cointegrates with pBM45
Figure 7C:
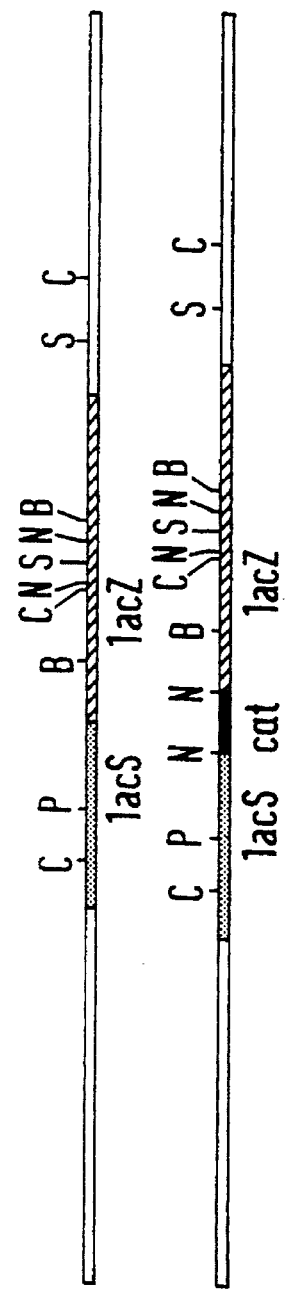
FIG. 7(c) illustrates the ones of the two possible, identified resolution end products from both cointegrates. Vector plasmid DNA originating from E. coli is shown as simple line. Restriction sites are: B, BglII; C. ClaI; N, NdeI; P, PstI; and S, SpeI.

Plasmid pBM45 was transformed into S. thermophilus ST11 by making use of the optimized transformation procedure as described above. Upon selection on M17 agar plates supplemented with 1% sucrose and 2.5 μg/ml erythromycin, about 1–10 colonies per 1 μg of transformed plasmid appeared after 2–3 days of anaerobic incubation at 42° C. Single colonies were isolated, purified on fresh agar plates and grown in M17 broth complemented with 1% sucrose and 2.5 μg/ml erythromycin. Cells were harvested by centrifugation and their genomic DNA extracted as described above. Southern blots of PstI, ClaI, NdeI and PstI-BglII digested genomic DNA were performed. As labelled DNA probes we used plasmid pBM45, pBM32 and the 670 bp NdeI fragment from pBM40 containing the cat gene, respectively. Analysis of the different Southern blots confirmed formation of cointegrates between plasmid and bacterial genome. In all analyzed cases, integration of the plasmid took place at homologous DNA stretches between the plasmid and the genome, mediated by general recombination (FIG. 7).

ii) resolution of cointegrates

Overnight cultures of purified ST11 strains carrying cointegrates originating from pBM45 integrations were subcultivated by inoculating 40 ml of fresh M17, containing 1% lactose and no erythromycin, with 100 μl of the culture and incubated at 42° C. After cell growth reached saturation, subcultivation of the cultures was repeated in the same way and the cells grown again at 42° C. to saturation. This subcultivation procedure was repeated in total 15 times and thereafter, cells were diluted, spread onto M17 plates and incubated at 42° C. The next day, individual colonies were transferred to new M17 plates, with and without 5 μg/ml erythromycin, and incubated at 42° C. overnight. Cells from erythromycin sensitive colonies were transferred to M17 broth, grown at 42° C. and genomic DNA extracted therefrom as described earlier. The genomic DNA was digested with PstI, NdeI and PstI-Bg! II, size fractionated by agarose gel electrophoresis and transferred to GeneScreen hybridization membranes. DNA-DNA hybridizations according to Southern [Southern E. 1975. J. Mol. Biol. 98:503–517] were performed with either using pBM32, pBM45 or the 670 bp NdeI carrying the cat gene as DNA probe. The results confirmed that resolution of the cointegrates resulted in a complete loss of the plasmid backbone, including its erythromycin resistance gene, and one copy of the homologous repeated DNA sequence. Thus, depending on the location of the second recombination event, the lac operon was either reconstituted to its original wildtype configuration or replaced by the imported new operon structure (FIG. 7).

A strain isolated and identified as described above with containing the new operon structure, i.e. the cat gene integrated between the lacs and lacZ gene, is named ST11-Cat throughout the present specification and was deposited under the Budapest treaty on the 02.04.92 in the Collection National de Cultures de Microorganisme (CNCM) de l'Institut Pasteur, 25 rue de Docteur Roux, 75724 Paris Cedex 15, France, where it was given the number I-1190.

Stability of the integrated gene

80 μl of an overnight culture of strain ST11-Cat grown in M17 medium supplemented with 1% lactose was used to ]innoculate 80 ml of sterilized MSK and incubated at 42° C. After cell growth reached saturation, subcultivation of the culture was repeated consecutively 15 times with always transferring 80 μl of the homogenized milk culture into 80 ml of fresh MSK medium and growing the cells at 42° C. After these transfers, which correspond in total to about 150 generations of growth, cells were plated onto M17 agar plates supplemented with 1% lactose and incubated at 42° C. 300 individual colonies were picked onto M17 agar plates supplemented with 5 μg/ml chloramphenicol and incubated at 42° C. All analyzed colonies were able to grow on chloramphenicol plates and, thus, durably inherited the cat gene.

Activity of the integrated cat gene

ST11 and strain ST11-Cat were grown in MSK overnight at 42° C. The next day, 100 μl of each culture was transferred to 50 ml MSK and 50 ml MSK supplemented with 10 μg/ml chloramphenicol and incubated at 42° C. After 24 h, both strains, ST11 and ST11-Cat, did grow in MSK and coagulated the milk, whereas only strain ST11-Cat was able to grow in MSK with chloramphenicol and to coagulate the milk. ST11 was not able to grow even after prolonged incubation for 3 days at 42° C. The results are summarized in Table I.

TABLE I

| strain: | ST11 | ST11-Cat |
|---|---|---|
| MSK (no chloramphenicol) | growth | growth |
| MSK (10 μg/ml chloramphenicol) | no growth | growth | strain: ST11 ST11-Cat

ST11 and ST11-Cat were grown in 30 ml M17 broth supplemented with 1% lactose, 1% sucrose or 1% glucose with or without the addition of 0.5% galactose. Cells were grown to mid-log phase, harvested by centrifugation, washed twice with TE (50 mM TrisHCl pH 7.8, 2 mM EDTA) and resuspended in 1 ml TE. The cell suspensions were kept on ice and extracts were obtained by grinding the cells with glass beads (425–600 μm) on a vortex apparatus for 1 hour at 4° C. [El Abboudi M., et al. 1991. J. of Food Sci. 56:948–953]. Cell debris and glass beads were precipitated by centrifugation (13000 g for 15 min at 4° C. ) and the cell free supernatants were used to determine the specific chloramphenicol acetyl transferase activities according to the assay described by W. V. Shaw [Shaw W. V. 1975. Meth. Enzymol. 43:737–755]. The results are shown in Table II. The enzyme activities are given as units per mg total protein.

TABLE II

| growth medium | ST11 | ST11-Cat |
|---|---|---|
| lactose | 0.0 | 3.2 |
| sucrose | 0.0 | 0.6 |
| glucose | 0.0 | 0.8 |
| lactose + galactose | 0.0 | 3.8 |
| sucrose + galactose | 0.0 | 2.4 |

TABLE II-continued

| growth medium | ST11 | ST11-Cat |
|---|---|---|
| glucose + galactose | 0.0 | 3.6 |

EXAMPLE 2

Integration of the cat gene into the lac operon: alternative system with selection for correct cointegrate resolution.

In Example 1, appropriate resolution of the genome-plasmid cointegration structure can be found by time consuming screening and analysis of erythromycin sensitive descendants of originally erythromycin resistant transformants. This experimental step can be improved as demonstrated in Example 2.

By the same means of plasmid integration and resolution, we replaced the wild-type lacZ gene of ST11 with a derivative copy, having the stretch of DNA between the start of the gene (NdeI site) and its first EcoRI site (at nucleotide position 319; [Schroeder C. J., et al. 1991. J. Gen. Microbiol. 137:369–380]) deleted (FIG. 8). The resulting lacZ minus strain, ST11-ΔlacZ, served as new host cell for transformation.

As donor plasmid for integration, we used a construction analogous to pBM40, which has the homologous region up-stream the cat gene extended, to bias integration (i.e. the first recombination event) to happen preferentially at this locus.

Figure 9A:
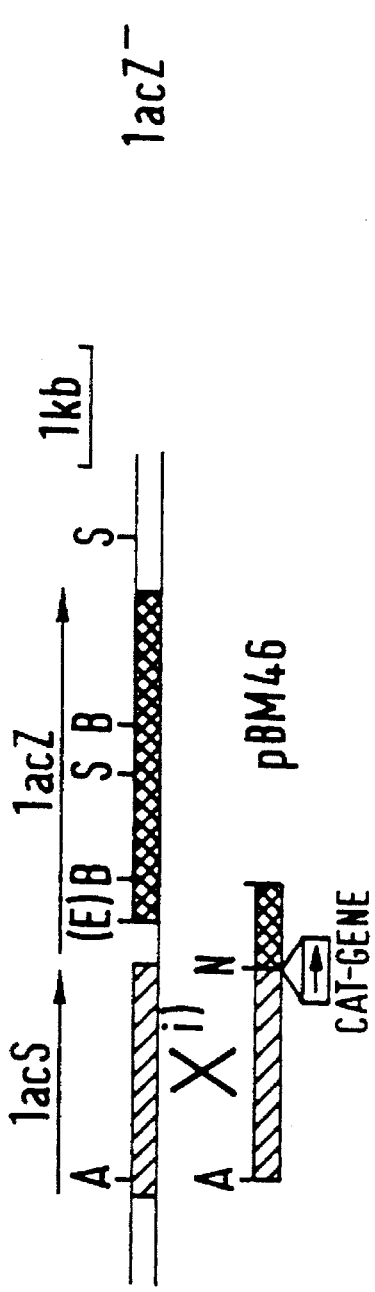
FIG. 9(a) represents the integration event of plasmid pBM46 into the genome of ST11-ΔlacZ via homologous recombination. The locus of this first recombination event (i) is marked by a cross.
Figure 9B:
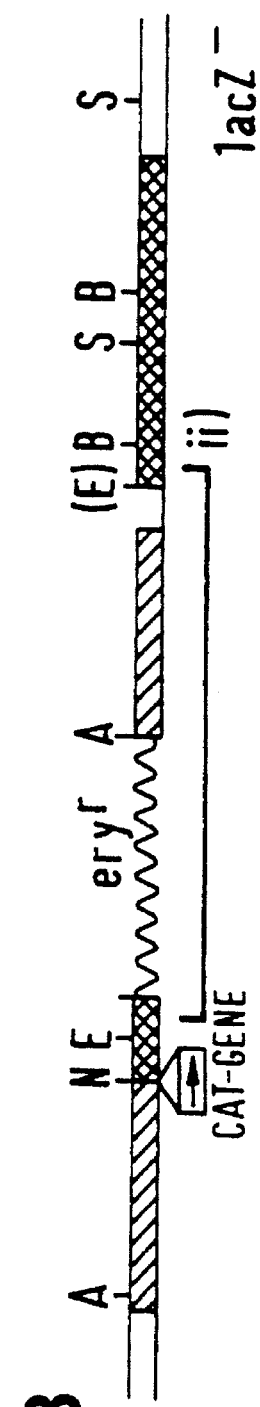
FIG. 9(b) represents the resulting cointegrate structure. The plasmid backbone sequence is shown as wavy line and the erythromycin resistance gene is indicated (ery). A bracket points to the second recombination event (ii) leading to resolution of the cointegrate structure.
Figure 9C:
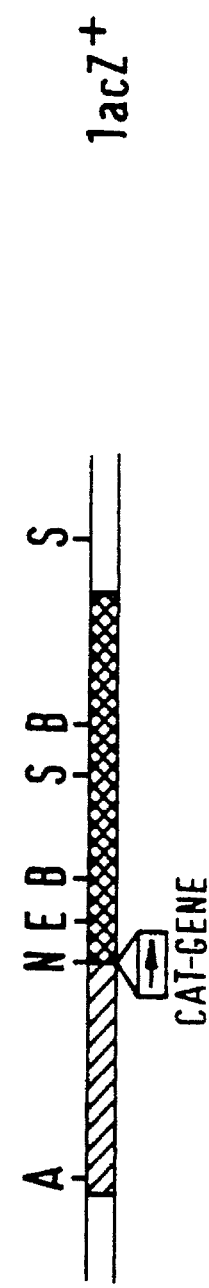
FIG. 9(c) shows the integrated cat gene following resolution-and the reconstituted lacZ gene. Restriction sites are as indicated in FIG. 8.

The new host was transformed with the constructed plasmid and erythromycin resistant colonies, which showed a lacZ minus phenotype on appropriate X-gal plates, were isolated and analysed. The resulting cointegrate structure of the integrated plasmid is presented in FIG. 9. Appropriate resolution (second recombination event down-stream the cat gene) will keep the cat gene inserted in the genome, eliminate the vector plasmid backbone carrying the erythromycin resistance gene and reconstitute the truncated lacZ gene (FIG. 9). Therefore, correct resolution can be selected for by growing cointegrate carrying cells in the absence of erythromycin in a lactose containing medium, e.g. milk.

For the whole experimental procedure, there was no need to select or screen for an activity produced by the gene to be integrated, i.e. in this example the cat gene. Therefore, any functional homo-, heterogenic or artifical gene, irrespective of its resulting phenotype can be integrated and expressed in this way. It will be stably maintained and its expression may be regulated by appropriate growth conditions.

Construction of donor plasmids i) pBM46

Plasmid pDP301 was digested with AatII, bluntended [Davis L. G., et al. 1986. Basic Methods in Molecular Biology, Elsevier Science Publishing Co., Inc., New York, N.Y., pp:240–243] and subsequently digested with BstEII. The ca. 1690 bp fragment carrying part of the lacS gene was isolated by agarose gel electrophoresis. Similarly, pBM40 was digested with PstI, bluntended [Davis L. G., et al. 1986. Basic Methods in Molecular Biology, Elsevier Science Publishing Co., Inc., New York, N.Y. pp:240–243], further digested with BstEII and the larger fragment comprising the vector backbone isolated by agarose gel electrophoresis. The two isolated fragments were ligated together according to standard procedures [Manitis T., et al. 1982. Molecular Cloning: A Labotratory, Cold Spring Harbor, N.Y.], transformed to BZ234 and put onto LB erythromycin (1 mg/ml) plates. After incubation at 37° C., single colonies were isolated and their plasmid content analysed. Correct clones were named pBM46 (FIG. 8).

ii) pBM49

Plasmid pBM46 was digested with EcoRI and NdeI, bluntended [Davis L. G., et al. 1986. Basic Methods in Molecular Biology, Elsevier Science Publishing Co., Inc., New York, N.Y.] and the largest fragment comprising the vector backbone isolated by agarose gel electrophoresis. It was subsequently religated on itself, transformed to BZ234 and the cells plated onto LB erythromycin (1 mg/ml) plates. After incubation, the plasmid content of single colonies was analysed and correct clones named pBM49 (FIG. 8).

Construction Of ST11-ΔlacZ

Plasmid pBM49 was transformed into S. thermophillus ST11 by making use of the optimized transformation procedure as described above. Upon selection on M17 agar plates supplemented with 1% sucrose and 2.5 µg/ml erythromycin, about 1–10 colonies per µg of transformed plasmid appeared after 2–3 days of anaerobic incubation at 42° C. Single colonies were isolated, purified on fresh agar plates and grown in M17 sucrose broth in the absence of erythromycin. The overnight cultures were diluted (1:50) into fresh identical broth and grown again to saturation. This subcultivation was repeated several times to ensure cell growth for over 30 generations in the absence of erythromycin. Thereafter, the cells were plated onto M17 sucrose plates containing 40 µg/ml X-gal and incubated under microaerophilic conditions (BBL CampyPak, Becton Dickinson & Co.). Single white colonies (lacZ minus; [Miller J. H. 1972. Experiments in Molecular Genetics. Cold Spring Harbor Laboratory, Cold Spring Harbor N.Y.] were picked and purified by restreaking and growing them for at least three times on agar plates. Then, they were tested for erythromycin sensitivity by restreaking onto M17 sucrose plates containing 2.5 µg/ml erythromycin. Cells with LacZ minus and erythromycin sensitive phenotype were identified, their genomic DNA was isolated and analysed by Southern blotting. Their expected genotype as presented in FIG. 9A was confirmed and the new strain was named ST11-ΔlacZ. It was deposited under the Budapest treaty on the 29.03.93 in the Collection National de Cultures de Microorganismes (CNCM) de l'Institut Pasteur, 25, rue de Docteur Roux, 75724 Paris Codex 15, France, where it was given the number I-1293.

Integration of the cat gene into the geonome of ST11-ΔlacZ i) cointegrate formation The procedure is the some as described for the cointegrate formation in Example 1. However, as donor plasmid pBM46 (instead of pBM45) and as host cell ST11-ΔlacZ (instead of ST11) was used. Erythromycin resistant transformants were lacZ minus as was determined on M17 agar plates con, raining 1% sucrose and 40 µg/ml X-gal.

ii) resolution of cointegrates

Single colonies were picked directly from the first selection plate (M17 agar with sucrose and erythromycin) after transformation of pBM46 and grown in 10 ml M17 medium supplemented with each 1% sucrose and lactose, in the absence of erythromycin. 1 ml of saturated culture was used to inoculate 100 ml MSK, which then was incubated at 42°C. for 1 to 2 days. After growth, cells were streaked onto M1.7 agar plates containing 1% sucrose, 1% lactose and 40 µg/ml X-gal and incubated under microaerophilic conditions at 42° C. Most to all colonies were blue, i.e. lacZ positive.

Single blue colonies were picked and tested for growth on agar plates containing either 2.5 µg/ml erythromycin or 10 µg/ml chloramphenicol. All tested colonies were erythromycin sensitive and chloramphenicol resistant. Southern blot analysis of their genomic DNA was performed and compared directly with DNA from ST11-Cat. All the results confirmed that the bacterial strains obtained in this way were identical to ST11-Cat.

---

We claim:

1. A process for integrating a promoterless foreign gene into the lac operon of *Streptococcus thermophilus* comprising:

transforming a host strain of *Streptococcus thermophilus* with a donor plasmid which does not replicate in the host strain, wherein the genome of the host strain includes a deletion within the lacZ gene which imparts a lac(−) phenotype to the host strain, and wherein the donor plasmid comprises a vector backbone and a sequence comprising a foreign gene lacking its native promoter operably integrated into at least a part of the lac operon of the host strain, in front of at least a part of the lacZ gene of the lac operon, wherein the donor plasmid comprises the fragment deleted from the lacZ gene of the host strain and wherein the sequence conserves the frame of the genomic lac operon of the host strain;

identifying cointegrate transformants in which the complete donor plasmid is integrated into the genomic lac operon of the host strain; and subcultivating identified cointegrate transformants an screening for lac(+) phenotype to identify an integrant transformant, the genome of which does not include the vector backbone of the donor plasmid but does include the foreign gene, which is operably integrated in front of the lacZ gene of the conserved genomic lac operon and which is stably maintained and expressed upon selective pressure on expression of the lacZ gene.

2. A process according to claim 1 wherein the deletion in the lacZ gene of the host strain is between the start of the lacz gene and its first EcoRI site.

3. A process according to claim 1 wherein the host strain is *S. thermophilus* CNCM I-1293.

4. A process according to claim 1 wherein the donor plasmid is pBM46.

5. A process according to claim 1 wherein the host strain is transformed by electroporation.

6. A process according to claim 1 wherein the foreign gene is of homogenic, heterogenic or synthetic origin, or of a combination thereof.

* * * * *

UNITED STATES PATENT AND TRADEMARK OFFICE
CERTIFICATE OF CORRECTION

PATENT NO. : 5,491,079
DATED : February 13, 1996
INVENTOR(S) : Jan KNOL, et al.

It is certified that error appears in the above-identified patent and that said Letters Patent is hereby corrected as shown below:

On the title page: Item "[30] Foreign Application Priority Data", "92105973" should be --92105973.9--.

On the title page under the heading "ABSTRACT", in line 11 of the abstract, "geonomic" should be --genomic--.

Column 16, line 62 (line 21 of claim 1), "an screening" should be --and screening--.

Signed and Sealed this

Twenty-fifth Day of June, 1996

Attest:

*Attesting Officer*

BRUCE LEHMAN
*Commissioner of Patents and Trademarks*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:1:

GGTTTTCCCA GTCACGAC                 18

( 2 ) INFORMATION FOR SEQ ID NO:2:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:2:

```
GTCATGTTCA TATGTTATTC TCCTTT                                                              26
```

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
AAAGGAGAAT AACATATGAA CATGAC                                                              26
```

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
TTGGGAGCTC TCCCTTAACA AAGAGA                                                              26
```

( 2 ) INFORMATION FOR SEQ ID NO:5:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
ATATCATATG AACTTTAATA AAATTGAT                                                            28
```

( 2 ) INFORMATION FOR SEQ ID NO:6:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
ATTATCATAT GTTATAAAAG CCAGTCATTA G                                                        31
```